United States Patent
Su

(10) Patent No.: US 8,927,572 B2
(45) Date of Patent: Jan. 6, 2015

(54) CRYSTAL FORM I OF SALT OF A DIPEPTIDYL PEPTIDASE-IV INHIBITOR AND PREPARATION METHOD AND USE THEREOF

(75) Inventor: Chutian Su, Jinan (CN)

(73) Assignee: Xuanzhu Pharma Co., Ltd., Shandong (CN)

( * ) Notice: Subject to any disclaimer, the term of this patent is extended or adjusted under 35 U.S.C. 154(b) by 0 days.

(21) Appl. No.: 14/127,824

(22) PCT Filed: Jul. 6, 2012

(86) PCT No.: PCT/CN2012/078294
§ 371 (c)(1),
(2), (4) Date: Mar. 28, 2014

(87) PCT Pub. No.: WO2013/007167
PCT Pub. Date: Jan. 17, 2013

(65) Prior Publication Data
US 2014/0206874 A1 Jul. 24, 2014

(30) Foreign Application Priority Data
Jul. 9, 2011 (CN) .......................... 2011 1 0202157

(51) Int. Cl.
C07D 401/14 (2006.01)
A61K 31/444 (2006.01)
C07D 471/04 (2006.01)
(52) U.S. Cl.
CPC ............ C07D 471/04 (2013.01); C07D 401/14 (2013.01); A61K 31/444 (2013.01)
USPC .......................................... 514/303; 546/118
(58) Field of Classification Search
CPC ...................... C07D 401/14; A61K 31/444
USPC .......................................... 514/303; 546/118
See application file for complete search history.

(56) References Cited

FOREIGN PATENT DOCUMENTS

| CN | 101228164 | | 7/2008 |
|---|---|---|---|
| WO | WO-2004050658 | | 6/2004 |
| WO | WO-2009099594 | | 8/2009 |
| WO | 2011085643 | * | 7/2011 |
| WO | WO-2011085643 | | 7/2011 |

* cited by examiner

Primary Examiner — Niloofar Rahmani
(74) Attorney, Agent, or Firm — Cesari and McKenna, LLP; Y. Rocky Tsao

(57) ABSTRACT

The present invention relates to the crystal form I of salt of a dipeptidyl peptidase-IV inhibitor, and the preparation method and use thereof. In particular, it relates to the crystal form I of dihydrochloride salt of the compound (R)-2-[[7-(3-aminopiperidin-1-yl)-3,5-dimethyl-2-oxo-2,3-dihydro-1H-imidazo[4,5-b]pyridin-1-yl]methyl]benzonitrile represented by formula (1), which is a dipeptidyl peptidase-IV inhibitor, and the preparation method and use thereof. The crystal form I of dihydrochloride salt of the dipeptidyl peptidase-IV inhibitor represented by formula (1) is characterized in that it has characteristic peaks at 8.7±0.2°, 19.4±0.2°, 23.5±0.2° and 27.2±0.2° in X-ray powder diffraction indicated by an angle 2θ (°) using Cu—Kα irradiation.

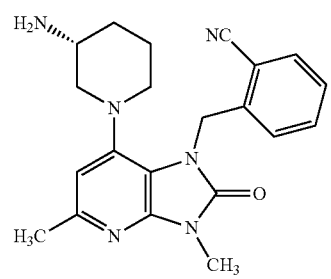

(1)

18 Claims, 1 Drawing Sheet

CRYSTAL FORM I OF SALT OF A DIPEPTIDYL PEPTIDASE-IV INHIBITOR AND PREPARATION METHOD AND USE THEREOF

CROSS-REFERENCE TO RELATED APPLICATIONS

This application is the National Stage of International Application No. PCT/CN2012/078294 filed on Jul. 6, 2012, which claims the benefit of Chinese Patent Application 201110202157.9 filed on Jul. 9, 2011. The contents of both applications are hereby incorporated by reference in their entirety.

TECHNICAL FIELD

The present invention belongs to the field of medicinal technology, and specifically relates to crystal form I of salt of a dipeptidyl peptidase-IV inhibitor, and the preparation method and use of the same.

BACKGROUND ART

Dipeptidyl peptidase-IV (DPP-IV) inhibitors are a new generation of peroral drugs for treating type 2 diabetes and act by enhancing the activity of incretin, belonging to non-insulin therapeutical drugs. Compared to conventional drugs for treating diabetes, DPP-IV inhibitors have no adverse effects such as weight gain and edema etc.

The compound (R)-2-[[7-(3-aminopiperidin-1-yl)-3,5-dimethyl-2-oxo-2,3-dihydro-1H-imidazo[4,5-b]pyridin-1-yl]methyl]benzonitrile represented by formula (1) (hereinafter, referred as Compound A, which was described in the patent application CN201010291056.9) is a DPP-IV inhibitor compound, and has a strong inhibitory effect and a very high selectivity for DPP-IV.

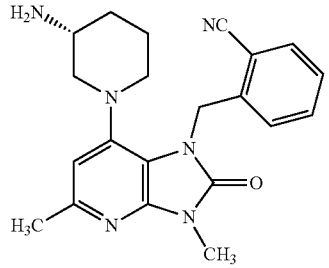

Formula (1)

In the research and development of medicines, the study on crystal forms is very important, and different crystal forms of a compound will result in different properties such as stability and solubility etc. Accordingly, after extensive investigation on the crystal forms of Compound A or salts thereof, the present inventors have found and identified crystal forms of a salt of Compound A.

SUMMARY OF THE INVENTION

The object of the present invention is to solve the above-mentioned problems and provide crystal forms of Compound A or a salt thereof having better stability and operability, good bioavailability and solubility, and the preparation method thereof.

The present invention provides crystal form I of dihydrochloride salt of Compound A represented by formula (1): the crystal form I has characteristic peaks at 8.7±0.2°, 19.4±0.2, 23.5±0.2° and 27.2±0.2° in X-ray powder diffraction indicated by an angle 2θ (°) using Cu—Kα irradiation.

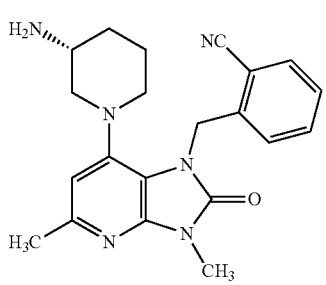

Formula (1)

The crystal form I of dihydrochloride salt of Compound A also has, in addition to the above characteristic peaks, characteristic peaks at 12.5±0.2°, 22.5±0.2° and 25.5±0.2° in X-ray powder diffraction indicated by an angle 2θ (°) using Cu—Kα irradiation.

The crystal form I of dihydrochloride salt of Compound A also has, in addition to the above characteristic peaks, characteristic peaks at 11.7±0.2°, 14.6±0.2° and 26.0±0.2° in X-ray powder diffraction indicated by an angle 2θ (°) using Cu—Kα irradiation.

The present invention also provides a method for preparing the crystal form I of dihydrochloride salt of Compound A.

The crystal form I of dihydrochloride salt of Compound A is obtained by dissolving Compound A in an organic solvent and increasing the temperature, then adding dropwise hydrochloric acid in a certain stoichiometric ratio thereto, thereafter stirring, filtering and drying.

The "organic solvent" used for dissolving Compound A in the above preparation method is selected from lower alcohols containing 1-4 carbon atom(s), such as methanol, ethanol, propanol, isopropanol, n-butanol, isobutanol or the like; lower ketones containing 3-6 carbon atoms, such as acetone, butanone or the like; acetonitrile; propionitrile; tetrahydrofuran or the like. Among them, ethanol is preferable.

The "organic solvent" used for dissolving Compound A in the above preparation method also can be a mixed solvent. The mixed solvent refers to a mixed solvent consisting of two or more organic solvents in a certain volume ratio, or a mixed solvent consisting of an organic solvent and water in a certain volume ratio. The mixed solvent includes, but not limited to, the following mixed solvent systems and the ratios thereof: methanol/water (40:1), ethanol/water (40:1), acetonitrile/water (25:1), tetrahydrofuran/water (40:1), acetone/water (30:1), 1,4-dioxane/water (25:1) and the like; methanol/acetonitrile, methanol/tetrahydrofuran, methanol/dichloromethane, methanol/ethyl acetate, methanol/methyl tert-butyl ether, methanol/n-hexane, methanol/toluene, ethanol/acetonitrile, ethanol/tetrahydrofuran, ethanol/dichloromethane, ethanol/ethyl acetate, ethanol/methyl tert-butyl ether, ethanol/n-hexane, ethanol/toluene, isopropanol/acetonitrile, isopropanol/tetrahydrofuran, isopropanol/dichloromethane, isopropanol/ethyl acetate, isopropanol/methyl tert-butyl ether, isopropanol/n-hexane, isopropanol/toluene, acetonitrile/methyl tert-butyl ether, acetonitrile/ethyl acetate, acetonitrile/dichloromethane, acetonitrile/tetrahydrofuran, acetonitrile/n-hexane, acetonitrile/toluene, methyl tert-butyl ether/ethyl acetate, methyl tert-butyl ether/dichloromethane, methyl tert-butyl ether/tetrahydrofuran, methyl tert-butyl ether/n-hexane, methyl tert-butyl ether/toluene, ethyl acetate/dichloromethane, ethyl acetate/tetrahydrofuran, ethyl acetate/n-hexane, ethyl acetate/toluene, dichloromethane/tetrahydrofuran, dichloromethane/n-hexane, dichloromethane/toluene, tetrahydrofuran/n-hexane, tetrahydrofuran/toluene, n-hexane/toluene (the mixed volume ratio of the above solvents being 1:1) and the like. The mixed solvent is preferred to be a mixed solvent consisting of two or more organic solvents of "lower alcohols containing 1-4 carbon atom(s), such as methanol, ethanol, propanol, isopropanol, n-butanol, isobutanol or the like; lower ketones containing 3-6 carbon atoms, such as acetone, butanone or the like; acetonitrile; propionitrile; and tetrahydrofuran or the like" in a certain volume ratio, or a mixed solvent consisting of these organic solvents and water in a certain volume ratio. The mixed solvent of ethanol/water is more preferred.

The phrase "in a certain stoichiometric ratio" mentioned in the above preparation method refers to the molar ratio between Compound A and hydrochloric acid is ≤1:2, preferably in the range of from 1:4 to 1:2.

The present invention also provides a pharmaceutical composition comprising the crystal form I of dihydrochloride salt of Compound A and one or more pharmaceutically acceptable carriers and/or diluents, which can be orally administered to patients in need of such treatment. When it is prepared into an oral formulation, suitable fillers, binders, disintegrating agents, lubricants and the like can be added.

The present invention also provides use of the crystal form I of dihydrochloride salt of Compound A in the manufacture of a medicament for treating and/or preventing non-insulin dependent diabetes.

DETAILED EMBODIMENTS

The present invention will be described in detail below by embodiments in a way of examples. However, it should be understood that the scope of the above subject matters of the present invention is not limited to the examples below only. All technical solutions carried out on the basis of the above disclosure of the present invention belong to the scope of the present invention.

Example 1

Preparation of the Crystal Form I of Dihydrochloride Salt of Compound A

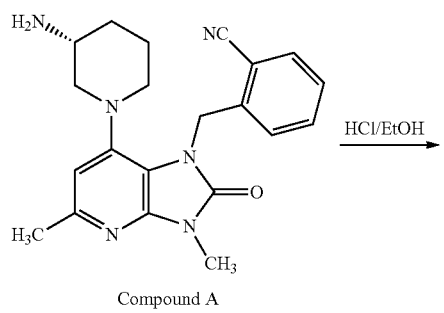

Compound A

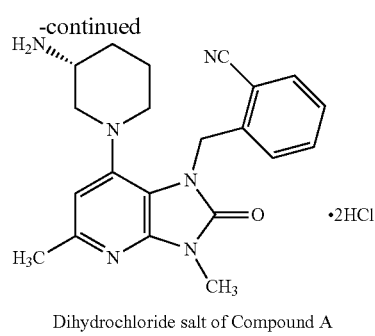

Dihydrochloride salt of Compound A 100 g Compound A (0.27 mol) was added into a three-necked flask, and 500 mL ethanol was added thereto. The temperature was increased to 60° C. via an oil bath. Then, 49.5 mL concentrated hydrochloric acid (12 mol/L) was added dropwise. Thereafter, the reaction mixture was stirred for 1 h and cooled down to room temperature, then further stirred for 1 h. After filtration and drying under vacuum at 35° C., 70 g crystal form I of dihydrochloride salt of Compound A (yield: 58.6%) was obtained.

Measurement for the Crystal Form I Obtained by the Above Method:

(1) Measurement by X-Ray Powder Diffraction

The conditions for the X-ray powder diffraction measurement were: Cu—Kα line, 1.54 Å (monochromator), measured by D/MAX-RB type X-ray diffractometer.

In X-ray powder diffraction indicated by an angle 2θ (°) using Cu—Kα irradiation, there were the characteristic peaks at 8.7±0.2°, 19.4±0.2°, 23.5±0.2° and 27.2±0.2°; also the characteristic peaks at 12.5±0.2°, 22.5±0.2° and 25.5±0.2°; and also the characteristic peaks at 11.7±0.2°, 14.6±0.2° and 26.0±0.2°.

Figure 1:
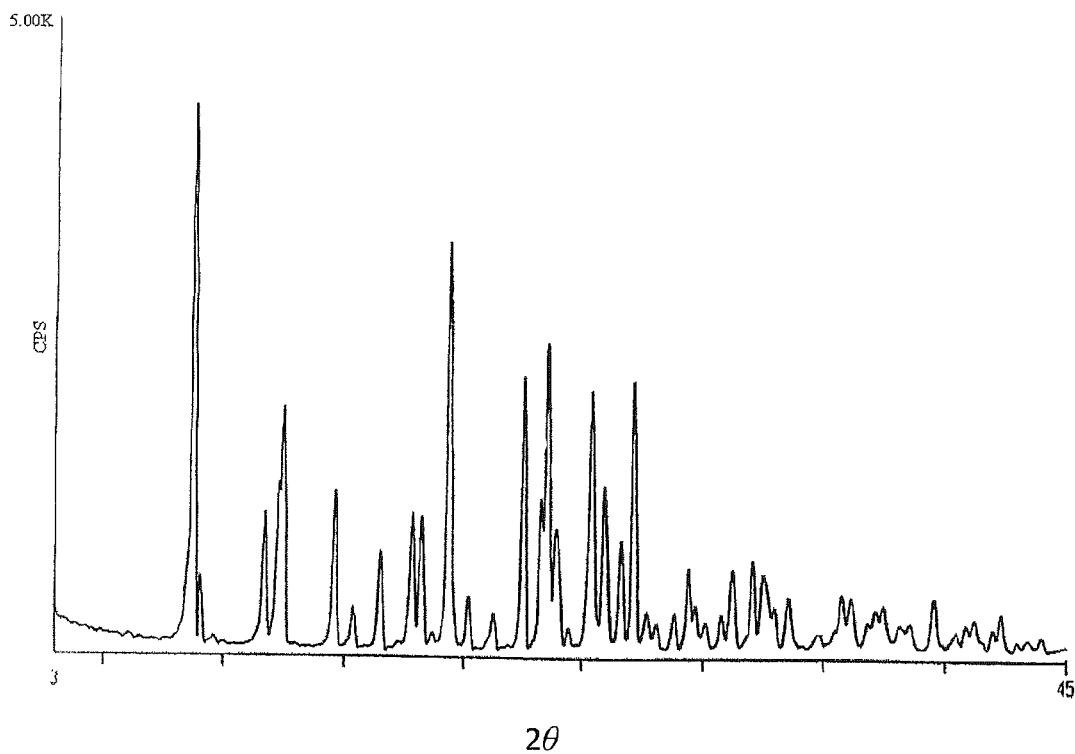
FIG. 1 is the X-ray powder diffraction pattern of the crystal form I of dihydrochloride salt of Compound A, wherein the ordinate represents the diffraction intensity (CPS) and the abscissa represents the diffraction angle (2θ).

When the crystal form of the present invention was measured via the X-ray powder diffraction, sometimes there were measuring errors in the peaks measured due to the measuring instrument or conditions used. Accordingly, when determining the crystal structure, such errors should be considered. Thus, an error range (±0.2°) was considered when determining the 2θ angles in the present invention. Regarding the X-ray powder diffraction: the X-ray powder diffraction diagram was shown in FIG. 1, wherein the crystal form I had peaks at the following diffraction angles 2θ (°): 8.70°, 11.66°, 12.46°, 14.62°, 19.38°, 22.50°, 23.52°, 25.42°, 26.00° and 27.14°.

(II) Measurement by X-Ray Single Crystal Diffraction

The conditions for the single crystal diffraction measurement were:

Type of Instrument: Oxford Xcalibur, Eos, Gemini: versatile dual-source system (universal double sources system).

Light Source of Diffraction: 'Cu—Kα'

Analysis Method of Single Crystal: direct method

Refinement Method of Structure: full-matrix least-square method (SHELX-97)

Figure 2:
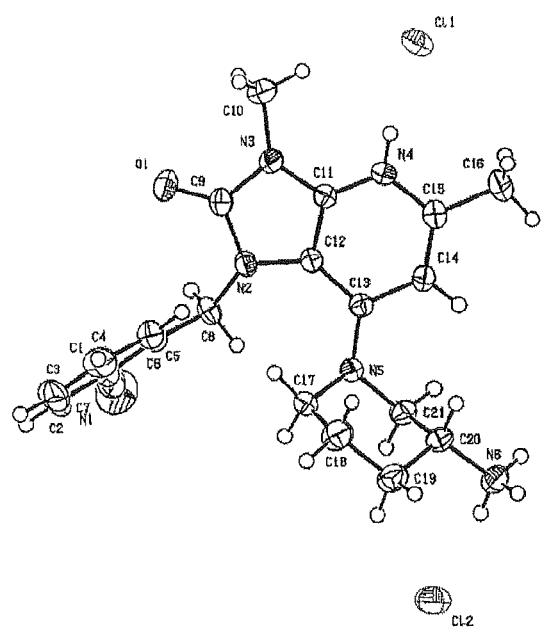
FIG. 2 is a single molecular structure diagram in the X-ray single-crystal diffraction of the crystal form I of dihydrochloride salt of Compound A.

The molecular structure diagram of the crystal form I according to the single-crystal diffraction was shown in FIG. 2. The lattice parameters were as follows:

| Parameters | | Values |
|---|---|---|
| Crystal system | | Orthogonal |
| Space Group | | P2$_1$2$_1$2$_1$ |
| Lattice parameters | a [Å] | 10.2064(4) |
| | b [Å] | 11.0404(4) |

-continued

| Parameters | Values |
| --- | --- |
| c [Å] | 19.9620(7) |
| α [°] | 90 |
| β [°] | 90 |
| γ [°] | 90 |
| Lattice volume (V) [Å³] | 2249.38(14) |
| Z (molecule number in single lattice) | 4 |
| Density calculated [g/cm³] | 1.327 |

Note:
Cl1 and Cl2 in FIG. 2 represent two HCls.

Example 2

Investigation on the Water Solubility of Crystal Form I of Dihydrochloride Salt of Compound A

TABLE 1

| Solubility | |
| --- | --- |
| Test samples | Water solubility |
| Compound A | <0.1 mg/ml |
| Crystal form I of Dihydrochloride salt of Compound A | >1 g/ml |

As seen from above, Compound A has a very poor water solubility and is hardly dissolved or insoluble in water. On the contrary, the crystal form I of dihydrochloride salt of Compound A can be dissolved very easily in water, and the bioavailability thereof is high by oral administration.

Example 3

Investigation on the Stability of Crystal Form I of Dihydrochloride Salt of Compound A Test Sample:
The crystal form I of dihydrochloride salt of Compound A prepared from Example 1.

The Test Conditions for Investigating the Influencing Factors:

Each of the test samples was placed at a high temperature of 60° C. (packed with an plastic bag for packing drugs as the inner layer and an aluminium foil as the outer layer), a high humidity of RH75%±5% (uniformly spread on a dry and clean watch glass), and a light irradiation of 4500 Lx±500 Lx (uniformly spread on a dry and clean watch glass). Sampling was performed on Day 5 and Day 10 respectively, and Relevant Substance and the content of Compound A were measured and compared with those of the sample on Day 0.

The Test Conditions for Investigating the Long-Term Stability:

Each of the test samples was placed at a temperature of 25° C.±2° C. and a humidity of RH 60%±10%. Sampling was performed at the end of Months 3, 6, 9, 12 and 18 respectively, and Relevant Substance and the content of Compound A were measured and compared with those of the sample on Day 0. During the investigation, the sample was packed with a plastic bag for packing drugs as the inner layer and an aluminium foil as the outer layer.

Measurement of Content

The content was measured by using an External Standard method in accordance with the High Performance Liquid Chromatography in Chinese Pharmacopoeia, Appendix V D, Edition 2010.

Measurement of Relevant Substance

The Relevant Substance was measured by using an Area Normalization method in accordance with the High Performance Liquid Chromatography in Chinese Pharmacopoeia, Appendix V D, Edition 2010.

The experimental results were shown in the tables below.

TABLE 2

The investigation results of the influence factor test

| Test conditions | Day | Properties | Content of Relevant Substance (%) | Content of Compound A (%) |
| --- | --- | --- | --- | --- |
| 60° C. | 0 | white crystalline powder | 0.151 | 99.16 |
| | 5 | white crystalline powder | 0.156 | 98.80 |
| | 10 | white crystalline powder | 0.142 | 99.42 |
| RH 75% ± 5% | 5 | white crystalline powder | 0.200 | 99.30 |
| | 10 | white crystalline powder | 0.171 | 99.55 |
| 4500Lx ± 500Lx | 5 | white crystalline powder | 0.194 | 98.09 |
| | 10 | white crystalline powder | 0.159 | 99.17 |

TABLE 3

The investigation results of the long-term stability Test

| Test sample | Month | Properties | Content of Relevant Substance (%) | Content of Compound A (%) |
| --- | --- | --- | --- | --- |
| Crystal Form I of dihydrochloride salt of Compound A | 0 | white crystalline powder | 0.211 | 99.53 |
| | 3 | white crystalline powder | 0.251 | 99.32 |
| | 6 | white crystalline powder | 0.246 | 99.19 |
| | 9 | white crystalline powder | 0.248 | 98.99 |
| | 12 | white crystalline powder | 0.221 | 99.17 |
| | 18 | white crystalline powder | 0.221 | 99.37 |

The inventors have investigated the stability of the crystal form I of dihydrochloride salt of Compound A. As seen from the experimental results, in the crystal form I of dihydrochloride salt of Compound A under the conditions of high temperature, high humidity and light irradiation as well as in the long-term stability investigating test, Relevant Substance and the content of Compound A were substantially unchanged. It shows that the crystal form I of dihydrochloride salt of Compound A has a higher stability, which is convenient for the preparation, storage and transport of medicines, and the long validity period is benefit to ensure the effectiveness and safety in medicine usage.

Example 4

Pharmacological Experiment of the Crystal Form I of Dihydrochloride Salt of Compound A Test sample: the crystal form I of dihydrochloride salt of Compound A prepared from Example 1.
Experimental animals: Mice C57BL/6, quantity 40.

Test Method:

On the day before the test, the food for mice was removed at 5 p.m., and the mice were fasted overnight. On the second day, the fasting blood glucose of each mouse was checked at 9 a.m. and recorded as −30 min blood glucose. The body weight was weighed and recorded. After balancing the blood glucose level and body weight, the mice were randomly divided into four groups, namely Background Control group, Vehicle Control group, Dosing group 1 and Dosing group 2. To the later three groups, a vehicle (0.9% sodium chloride injection solution), 1 mg/kg test sample and 3 mg/kg test sample was administered respectively, and the volume administered was 10 mL/kg. The blood glucose of each mouse was measured and recorded as 0 min blood glucose 30 minutes after the intragastric administration. Afterwards glucose was further administered via intragastric administration at a dose of 3 g/kg to the Vehicle Control group, Dosing group 1 and Dosing group 2, and 0.9% sodium chloride injection solution was administered via intragastric administration to the Background Control group at an intragastric administration volume of 10 mL/kg. Then, the blood glucose levels were measured at 20, 40, 60 and 120 minutes after the administration of glucose or sodium chloride solution.

Analysis and Processing of the Data:

The area under the time-blood glucose curve of the OGTT (Oral Glucose Tolerance Test) (AUC) was calculated. A net variable AUC (ΔAUC) was obtained by subtracting the AUC of Background Control group from that of Vehicle Control group, Dosing groups 1 and 2. The inhibition ratio (%)=100× ($\Delta AUC_{Vehicle\ Control\ group}$-ΔAUC)/$\Delta AUC_{Vehicle\ Control\ group}$, wherein ΔAUC is the net variable AUC of each Dosing group, and $\Delta AUC_{Vehicle\ Control\ group}$ is the net variable AUC of Vehicle Control group. The data of Dosing groups were compared with that of Vehicle Control group by using t-test value analysis, and the difference was considered significant at $p<0.05$.

Results: The inhibition ratios for the blood glucose AUC were 57% and 65%, respectively when administering the test samples at 1 mg/kg or 3 mg/kg.

Conclusion: The crystal form I of dihydrochloride salt of Compound A has a significant effect for reducing blood glucose, and thus can be used for treating and/or preventing non-insulin dependent diabetes.

Example 5

In Vivo Study on the Pharmacokinetics of Crystal Form I of Dihydrochloride Salt of Compound A in SD Rats Test sample: the crystal form I of dihydrochloride salt of Compound A prepared from Example 1.

Experimental Animals: SD (Sprague Dwaley) rats, quantity 12.

Method:

The SD rats were divided into two groups, namely Intravenous Injection group and Intragastric Administration group, and there were 6 rats in each group in which one half were female and the other were male. The dose administrated was always 10 mg/kg (in terms of Compound A). The volume administered by the intravenous injection route was 5 mL/kg, and the volume administered by the intragastric administration route was 10 mL/kg. The time points for sequential blood sampling were 0 minutes before administration (0 min), and 5 min, 15 min, 30 min, 1 h, 2 h, 4 h, 6 h, 8 h, 12 h and 24 h after administration. About 150 μL of blood was collected into a sodium heparin anticoagulation tube from the caudal vein or Inner canthus vein after administration. The whole blood was placed in a high-speed refrigerated centrifuge (8000 rpm, 0-4° C.) and centrifuged for 6 min. The supernatant of the blood plasma was separated and stored in a refrigerator for measurement. The centrifugation of all blood samples was completed within 30 min after blood collection. The concentration of Compound A in the blood plasma of SD rats was determined by LC-MS/MS method.

Analysis and processing of Data: The plasma concentration—time curve was plotted, and the pharmacokinetic parameters were calculated by using the non-compartment model in Phrsight Phoenix 6.1.

Results: The plasma clearance (CL) of SD rats after intravenous injection administration was 2.40 L/h/kg, the apparent volume of distribution (Vd) was 6.17 L/kg, and the bioavailability (F %) was 96.56%.

Conclusions: The in vivo bioavailability of the crystal form I of dihydrochloride salt of Compound A in SD rats is high, the clinical dose administrated is low and the cost for treatment will be saved significantly.

The invention claimed is:

1. A crystal form I of dihydrochloride salt of the compound (R)-2-[[7-(3-aminopiperidin-1-yl)-3,5-dimethyl-2-oxo-2,3-dihydro-1H-imidazo[4,5-b]pyridin-1-yl]methyl]benzonitrile represented by formula (1), wherein its characteristic peaks at 8.7±0.2°, 19.4±0.2°, 23.5±0.2° and 27.2±0.2° in X-ray powder diffraction indicated by an angle 2θ(°) using Cu—Kα irradiation,

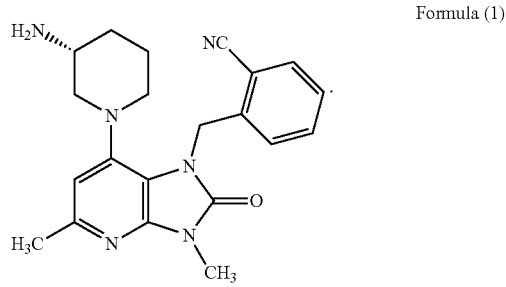 [SMILES: Cc1cc(N2CCC[C@@H](N)C2)c2c(n1)n(C)c(=O)n2Cc1ccccc1C#N]

Formula (1)

2. The crystal form I according to claim 1, wherein by its characteristic peaks at 12.5±0.2°, 22.5±0.2° and 25.5±0.2° in X-ray powder diffraction indicated by an angle 2θ(°) using Cu—Kα irradiation.

3. The crystal form I according to claim 2, wherein by its characteristic peaks at 11.7±0.2°, 14.6±0.2° and 26.0±0.2° in X-ray powder diffraction indicated by an angle 2θ(°) using Cu—Kα irradiation.

4. A preparation method for the crystal form I according to claim 1, comprising in that dissolving the compound (R)-2-[[7-(3-aminopiperidin-1-yl)-3,5-dimethyl-2-oxo-2,3-dihy-dro-1H-imidazo[4,5-b]pyridin-1-yl]methyl]benzonitrile in an organic solvent and increasing the temperature, then adding dropwise hydrochloric acid in a certain stoichiometric ratio thereto, thereafter stirring, filtering and drying to obtain the crystal form I of dihydrochloride salt of the compound.

5. The preparation method according to claim 4, comprising the organic solvent is selected from lower alcohols containing 1-4 carbon atom(s), lower ketones containing 3-6 carbon atoms, acetonitrile, propionitrile or tetrahydrofuran.

6. The preparation method according to claim 5, comprising the organic solvent is a lower alcohol containing 1-4 carbon atom(s) selected from methanol, ethanol, propanol, isopropanol, n-butanol or isobutanol.

7. The preparation method according to claim 6, comprising the organic solvent is ethanol.

8. The preparation method according to claim 4, comprising the organic solvent is a mixed solvent consisting of two or more organic solvents selected from lower alcohols containing 1-4 carbon atom(s), lower ketones containing 3-6 carbon atoms, acetonitrile, propionitrile or tetrahydrofuran.

9. The preparation method according to claim 8, comprising the organic solvent is an ethanol/water mixed solvent.

10. The preparation method according to claim 4, comprising the molar ratio of the compound (R)-2-[[7-(3-aminopiperidin-1-yl)-3,5-dimethyl-2-oxo-2,3-dihydro-1H-imidazo[4,5-b]pyridin-1-yl]methyl]benzonitrile to hydrochloric acid is less than or equals to 1:2.

11. The preparation method according to claim 10, comprising the molar ratio of the compound (R)-2-[[7-(3-aminopiperidin-1-yl)-3,5-dimethyl-2-oxo-2,3-dihydro-1H-imidazo[4,5-b]pyridin-1-yl]methyl]benzonitrile to hydrochloric acid is 1:4-1:2.

12. A pharmaceutical composition, wherein it includes the crystal formal I of dihydrochloride salt of the compound represented by formula (1) according to claim 1.

13. A preparation method for the crystal form I according to claim 2, characterized in that dissolving the compound (R)-2-[[7-(3-aminopiperidin-1-yl)-3,5-dimethyl-2-oxo-2,3-dihydro-1H-imidazo[4,5-b]pyridin-1-yl]methyl]benzonitrile in an organic solvent and increasing the temperature, then adding dropwise hydrochloric acid in a certain stoichiometric ratio thereto, thereafter stirring, filtering and drying to obtain the crystal form I of dihydrochloride salt of the compound.

14. A preparation method for the crystal form I according to claim 3, comprising dissolving the compound (R)-2-[[7-(3-aminopiperidin-1-yl)-3,5-dimethyl-2-oxo-2,3-dihydro-1H-imidazo[4,5-b]pyridin-1-yl]methyl]benzonitrile in an organic solvent and increasing the temperature, then adding dropwise hydrochloric acid in a certain stoichiometric ratio thereto, thereafter stirring, filtering and drying to obtain the crystal form I of dihydrochloride salt of the compound.

15. The preparation method according to claim 13, wherein the organic solvent is selected from lower alcohols containing 1-4 carbon atom(s), lower ketones containing 3-6 carbon atoms, acetonitrile, propionitrile or tetrahydrofuran.

16. The preparation method according to claim 14, wherein the organic solvent is selected from lower alcohols containing 1-4 carbon atom(s), lower ketones containing 3-6 carbon atoms, acetonitrile, propionitrile or tetrahydrofuran.

17. A pharmaceutical composition, wherein it includes the crystal formal I of dihydrochloride salt of the compound represented by formula (1) according to claim 2.

18. A pharmaceutical composition, wherein it includes the crystal formal I of dihydrochloride salt of the compound represented by formula (1) according to claim 3.

* * * * *

UNITED STATES PATENT AND TRADEMARK OFFICE
CERTIFICATE OF CORRECTION

PATENT NO.       : 8,927,572 B2  
APPLICATION NO.  : 14/127824  
DATED            : January 6, 2015  
INVENTOR(S)      : Shu Page 1 of 2

It is certified that error appears in the above-identified patent and that said Letters Patent is hereby corrected as shown below:

On the title page item [12], should read
--Shu--

On the title page item [75], should read
--Chutian Shu, Jinan (CN)--

In the claims

Column 8 line 44-47, claim 2, should read
--2. The crystal form I according to claim 1, wherein ~~by~~ its characteristic peaks at 12.5±0.2°, 22.5+0.2° and 25.5±0.2° in X-ray powder diffraction indicated by an angle 2θ(°) using Cu--Kα irradiation.--

Column 8 line 48-51, claim 3, should read
--3. The crystal form I according to claim 2, wherein ~~by~~ its characteristic peaks at 11.7±0.2°, 14.6±0.2° and 26.0±0.2° in X-ray powder diffraction indicated by an angle 2θ(°) using Cu--Kα irradiation.--

Column 8, line 52-59 claim 4, should read
--4. A preparation method for the crystal form I according to claim 1, comprising ~~in that~~ dissolving the compound (R)-2-[[7-(3-aminopiperidin-1-yl)-3,5-dimethyl-2-oxo-2,3-dihydro-1H-imidazop[4,5-b]pyridine-1-yl]methyl]benzonitrile in an organic solvent and increasing the temperature, then adding dropwise hydrochloric acid in a certain stoichiometric ratio thereto, thereafter stirring, filtering and drying to obtain the crystal form I of dihydrochloride salt of the compound.--

Column 9 and 10 line 23-3 claim 13, should read
--13. A preparation method for the crystal form I according to claim 2, comprising dissolving the compound (R)-2-[[7-(3-aminopiperidin-1-yl)-3,5-dimethyl-2-oxo-2,3-dihydro-1H-imidazop[4,5-

Signed and Sealed this
Twenty-sixth Day of January, 2016

Michelle K. Lee
*Director of the United States Patent and Trademark Office* b]pyridine-1-yl]methyl]benzonitrile in an organic solvent and increasing the temperature, then adding dropwise hydrochloric acid in a certain stoichiometric ration thereto, thereafter stirring, filtering and drying to obtain the crystal form I of dihydrochloride salt of the compound.--